(12) United States Patent
Leibfried

(10) Patent No.: US 7,694,591 B2
(45) Date of Patent: Apr. 13, 2010

(54) METHOD AND APPARATUS FOR EVALUATING A DOSING OPERATION

(75) Inventor: Thomas Leibfried, Neuenbürg (DE)

(73) Assignee: STRATEC BIOMEDICAL Systems AG (DE)

( * ) Notice: Subject to any disclaimer, the term of this patent is extended or adjusted under 35 U.S.C. 154(b) by 634 days.

(21) Appl. No.: 11/642,116

(22) Filed: Dec. 20, 2006

(65) Prior Publication Data

US 2007/0177986 A1 Aug. 2, 2007

(30) Foreign Application Priority Data

Dec. 20, 2005 (DE) .................. 10 2005 060 862

(51) Int. Cl.
*B01L 3/02* (2006.01)
*G01F 19/00* (2006.01)
(52) U.S. Cl. .................... 73/864.01; 73/1.74
(58) Field of Classification Search .............. 73/1.74, 73/37, 864.01, 864.34
See application file for complete search history.

(56) References Cited

U.S. PATENT DOCUMENTS

| 4,448,058 | A | * | 5/1984 | Jaffe et al. ............... 73/23.3 |
| 4,794,085 | A | | 12/1988 | Jessop et al. |
| 5,182,938 | A | * | 2/1993 | Merkel .................. 73/19.05 |
| 5,463,895 | A | | 11/1995 | Brentz |
| 5,488,854 | A | | 2/1996 | Kawanabe et al. |
| 5,488,874 | A | * | 2/1996 | Kawanabe et al. ........ 73/863.01 |
| 5,503,036 | A | * | 4/1996 | Nguyen et al. ........... 73/864.34 |
| 5,537,880 | A | * | 7/1996 | Takeda et al. ........... 73/864.25 |
| 5,540,081 | A | | 7/1996 | Takeda et al. |
| 6,094,966 | A | * | 8/2000 | Papen et al. ............... 73/1.74 |
| 6,119,533 | A | | 9/2000 | Gherson et al. |
| 6,121,049 | A | | 9/2000 | Dorenkott et al. |
| 6,158,269 | A | | 12/2000 | Dorenkott et al. |
| 6,370,942 | B1 | * | 4/2002 | Dunfee et al. .............. 73/37 |
| 6,484,556 | B1 | | 11/2002 | Jabobs et al. |
| 6,938,504 | B2 | * | 9/2005 | Camenisch ............ 73/864.01 |

FOREIGN PATENT DOCUMENTS

| DE | 44 21 303 | 12/1994 |
| DE | 693 26 773 | 3/2000 |
| DE | 696 32 506 | 6/2005 |
| EP | 0 658 769 | 6/1995 |
| EP | 0 682 258 | 11/1995 |

(Continued)

*Primary Examiner*—John Fitzgerald
(74) *Attorney, Agent, or Firm*—Cantor Colburn LLP

(57) ABSTRACT

During a method of evaluating a dosing operation, carried out by means of a dosing pump, for dosing a liquid medium in a vessel, filled at least partially with a gas, a pressure profile of the gas, present in the vessel, is detected at least periodically during the dosing operation. This pressure profile is compared with a desired value profile, prescribed for a control unit of the dosing pump, of the pump rate or pump output defining the dosing operation, and an evaluation result is issued in dependence on the comparison. In such case, the dosing operation is evaluated to be faulty or in need of correction when it is determined that the detected pressure profile over time with the prescribed pump rate or prescribed pump output lies outside a desired value range. A plurality of error conditions for the evaluation of the dosing operation are used, which consider the pressure development in a time window after a prescribed change in the defining pump rate or pump output.

31 Claims, 4 Drawing Sheets

FOREIGN PATENT DOCUMENTS

| | | |
|---|---|---|
| EP | 0 753 750 | 1/1997 |
| EP | 0 810 438 | 12/1997 |
| EP | 0 981 048 | 2/2000 |
| EP | 1 036 335 | 9/2000 |
| EP | 1 066 532 | 1/2001 |
| EP | 1 329 725 | 7/2003 |
| EP | 1 333 288 | 8/2003 |
| EP | 1 588 766 | 10/2005 |
| WO | WO 01/88549 | 11/2001 |
| WO | WO 02/059626 | 8/2002 |
| WO | WO 02/073215 | 9/2002 |

* cited by examiner

METHOD AND APPARATUS FOR EVALUATING A DOSING OPERATION

CROSS REFERENCE TO RELATED APPLICATIONS

The present application claims the priority under 35 U.S.C. §119(a) of German Patent Application No. 10 2005 060 862.0, filed on Dec. 20, 2005, the content of which is herein incorporated by reference in its entirety.

1. Field of the Invention

The invention relates to a method and an apparatus for evaluating a dosing operation, carried out by means of a dosing pump, for dosing a liquid medium, more especially for evaluating an aspirating and/or dispensing operation during the pipetting process, according to the preamble of claims 1 and 18.

2. Brief Discussion of Related Art

Dosing operations for dosing liquids are often a constituent part of mixing or analyzing methods, wherein exact doses of liquids are taken from quantities of liquid and, for example, mixed together. Such operations are the order of the day in chemical, pharmaceutical, medicinal and human biological methods, but they may also occur in other technical fields. Unidentified inaccurate liquid dosages can thus lead to results which are hazardous or even dangerous for the health of living beings, more especially human beings, when the use of such dosing operations in the pharmaceuticals sector alone is considered. On the other hand, unnecessary waste dosages are to be avoided in order not to waste unnecessarily valuable and sometimes only limited available substances. In this respect, there is a need to be able to evaluate liquid dosing operations as early as possible with the greatest possible reliability for their accuracy.

Basically, in the case of clinical analyzing apparatuses, the transfer of specific liquid volumes begins with an aspiration operation, wherein the liquid to be transferred is drawn, for example, into a disposable pipette or tip. This aspiration or intake can be disturbed by various factors, for example air bubbles in the vessel, inhomogeneity of the liquid caused by coaglutinates, technical errors in the system, such as leakages, etc. All of these factors lead to a deviation of the actual drawn-in volume from the desired drawn-in volume. In consequence, the detection of faulty aspiration operations but also dispense operations is essential for the reliability of such apparatuses. Hence, a desired development of a state variable such as, for example, the pressure or the temperature of the medium which is drawn-in and is to be metered, for example over time is checked.

From WO 01/88549 A1, which comes the closest to the invention, it is known to detect the pressure development during a dosing operation and, if necessary, to fix markers relating to the switching-on and switching-off of the dosing pump. On the basis of the pressure development resp. pressure curve, three different evaluation methods are carried out, into which the pump activity however is no longer input. In consequence, a set of data records is produced with a large number of time-dependent pressure and event indications, in order to analyze the process. Within the scope of a Pressure Shape Test, the number of turning points in the pressure curve during the entire dosing operation is checked. A Pressure Recovery Test checks as to how far the pressure recovers at the end of the aspiration operation, and a Pressure Difference Test checks the difference between the initial pressure and the final pressure. The times for these tests are not associated, however, with the activity of the dosing pump.

From WO 02/073215 A2, a method and an apparatus are known for evaluating a liquid dosing operation, wherein a continuous development, with respect to time, of a state variable during a dosing operation is compared with a predetermined state variable desired value range over the substantially total time of a dosing operation. In dependence on this desired/actual comparison, an evaluation result is issued as to how far the liquid dosing operation was successful or not. In addition, the beginning of the liquid dosing operation or machine state variables, such as the position of a piston in the vessel, can be detected. A correlation between the machine state and the measured state variable is not established. In consequence, error regions in fact result there from the machine state, but not other desired values. In consequence, the test mechanism always remains identical, since only the desired values are exchanged.

In a similar manner, in many other cited references, a monitoring of the dosing operation is effected by the most varied conditions, derived from the pressure development. Thus, EP 981 048 B1 calculates as the desired value a pressure integral via a part of a pressure profile, produced with a reference liquid, and compares this desired value subsequently with an appropriate actual pressure integral. From EP 1 036 335 A, certain conditions are known which, for the monitoring based on the pressure determination over time, define limit values for the initial rise in vacuum, the time until the initial fall in vacuum, the pressure before the rise, the pressure after the fall and the pressure difference. Also, a monitoring, based solely on a pressure monitoring, is effected in the patents U.S. Pat. No. 6,119,533 A, U.S. Pat. Nos. 6,121,049 A and 6,158,269 A, or as a fault monitoring means dependent on the final pressure according to EP 682 258 B1.

A fault monitoring means during aspiration through pressure monitoring during the immersion process up to a constant pressure is known from U.S. Pat. No. 5,463,895 A; a foam monitoring means with a pressure limit value is known from U.S. Pat. No. 5,488,854 A; and a monitoring means for monitoring coagulation clots is known from U.S. Pat. No. 5,540,081 A using a plurality of discrimination circuits for the pressure monitoring of various regions.

From EP 658 769 A1 and from the associated DE 693 26 773 T2, a leakage test is known through monitoring for abrupt pressure changes during the dispense operation. For this purpose, the pump internal pressure is checked preferably once daily, when the aspiration process is stopped, to see whether and how quickly it drops towards air pressure. In consequence, the pressure after aspiration is tested in isolation, but not the entire course of the pump activity.

From EP 753 750 B1 and from the associated DE 696 32 506 T2, it is known to set predetermined threshold values, mainly for checking the technical components, such as valves and pumps of a system, in dependence on the switching-on and switching-off of the pump. If the detected pressure lies outside the desired ranges, defined by the threshold values, error messages arise without taking into consideration the pressure development over time. A variation of the threshold values through various phases of the aspiration or intake operation is not provided.

Additional publications, which disclose pressure measuring apparatuses for this purpose, are EP 810 438 A2, EP 1 066 532 A1, EP 1 329 725 A2, EP 1 333 288 A2, EP 1 588 766 A1, U.S. Pat. No. 4,794,085 A, U.S. Pat. No. 6,484,556 B1, DE 44 21 303 A1, and WO 02/059 626 A1.

BRIEF SUMMARY OF THE INVENTION

The invention makes available an alternative possibility which permits a reliable evaluation of liquid dosing operations.

For this purpose, the development of the pressure or of the temperature of the gas is detected in the vessel, into which the medium is dosed, with a prescribed course of the pump output or pump rate of the dosing pump. This means that the pressure or the temperature of the medium is correlated with the pump rate or pump output, in order to generate thereby conditions which permit an evaluation of the dosing operation as correct, in need of correction or faulty. Since the system is not only based on the pressure or the temperature, but also on the pump rate or pump output of the dosing pump, the system works very reliably. The system can be adapted to various existing apparatuses, through the input of few limit values and/or determination variables of the dosing pump. In consequence, an adaptation to various system media, which are used for the aspiration operation, is possible without any problem, irrespective of whether the system medium is air (pneumatic) or completely liquid (hydraulic). The method and the apparatus are usable, as it were, when the system medium is in fact liquid, but air is in the vessel.

This can be further assisted by the use of a by-pass duct on the vessel, which permits an immediate measurement of pressure changes in the vessel without having to refer to measurements of changes in the liquid medium, with which the reduced pressure is produced in the vessel.

Additional advantages are found in the sub-claims and in the following description.

BRIEF DESCRIPTION OF THE FIGURES

The invention is explained more fully hereinafter with reference to the accompanying Figures. In the drawings.

DETAILED DESCRIPTION OF THE INVENTION

The invention is now explained more fully by way of example with reference to the accompanying drawings. However, the embodiments are only examples which should not limit the inventive concept to a specific arrangement.

Before the invention is described in detail, it is to be pointed out that it is not limited to the respective component parts of the apparatus or to the illustrated mode of operation within the scope of the method, since these component parts and methods may vary. The terms used here are only intended to describe particular embodiments, and are not used in a limiting manner. When, in the description and in the claims, the singular or indefinite articles are used, these terms also refer to the plurality of these elements, insofar as the overall context does not distinctly imply something else. The same applies conversely.

When the term "pressure" is used hereinafter in the description or in the claims, it is reduced pressure in this case, so that an increase in the pressure relates to an increase in the reduced pressure. Equally, in the Figures, the reduced pressure is plotted with reversed signs, that is to say plotted upwardly in a reducing manner, as the person skilled in the art in this field is used to doing.

Figure 1:
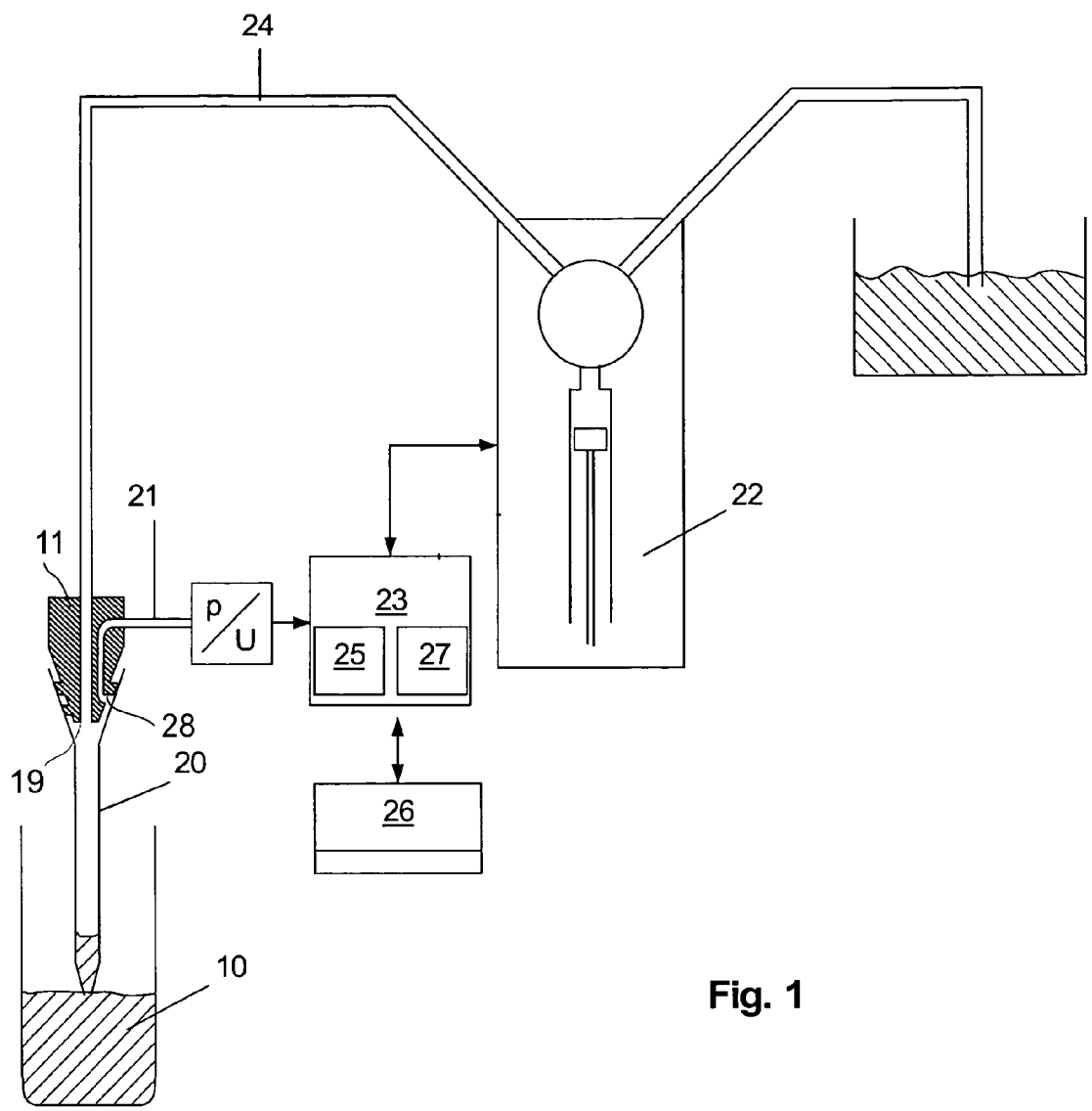
FIG. 1 is a schematic view of a dosing apparatus.

The apparatus illustrated schematically in FIG. 1 is used for dosing a liquid medium into a vessel 20, filled at least partially with a gas, preferably with air. The vessel 20 may be a disposable pipette. The dosing operation is more especially an aspirating and/or a dispensing operation, such as is used in a pipetting apparatus or system. Such dosing apparatuses are used for dosing preferably liquid media in chemical, pharmaceutical, medicinal and human biological methods and the like. It is significant, in this respect, to detect accurately the quantities to be metered and to recognize such, more especially, if a dosing operation ever fails for any reason.

The pressure p of the gas 10 present in the vessel 20 is detected via a sensor 21 at least periodically during the dosing operation, to produce a pressure development or course. The values thus determined are given to the control unit 23, which includes a data storage unit 25 for the determined values on the one hand and, on the other hand, a data processing unit 27. Via the dosing pump 22, a reduced pressure is produced in the vessel 20, by means of a system medium 24, which may be air or a liquid, in order to aspire liquid, or respectively a pressure is produced in order to dispense liquid again. The control unit communicates with the dosing pump 22 via a control line. In addition, the pump rate or pump output is prescribed at the control unit 23. With reference to the values prescribed, for example, as control variables for the dosing pump, the control unit 23 or the data processing unit respectively calculates evaluation criteria, which permit an evaluation as to whether the dosing operation is successful or not. The evaluation result can be issued on a read-out unit 26, for which any desirable apparatus is considered, which permits an interface with another apparatus or with the person by means of an acoustic or visual signal. Equally, a display on a display screen is possible.

If, instead of the pressure p, the temperature is detected, a comparable build-up is achieved with a temperature sensor instead of the pressure sensor. In consequence, when mention is made hereinafter of pressure, this term can be replaced by the term temperature, if reference thereto is not expressly made.

Figure 2:
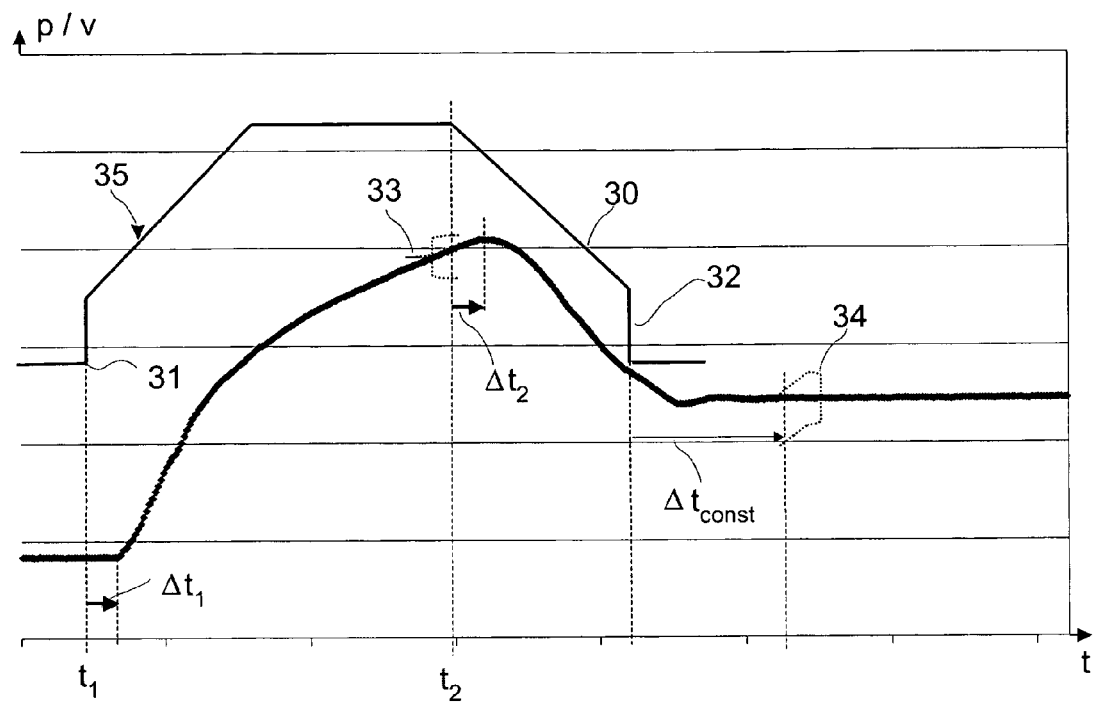
FIG. 2 illustrates a typical pressure development of an aspiration process, superimposed with the rate development of the pump.

A typical dosing operation basically shows the pressure curve illustrated in FIG. 2. Initially, the pressure is at ambient pressure up to the point in time $t_1$ when the tip of the vessel dips into the liquid. The pressure during the aspiration process and during the dispense process is referenced to this ambient pressure or—in better words—to the pressure that exists prior to the pump action. The starting of the dosing pump 22 then leads to a pressure increase. At this moment, the quantity of gas present in the vessel 20 is separated from the ambient air, and the pressure rises with a further pumping movement of the dosing pump 22, the suction pressure being added as the pressure at the tip of the disposable pipette. If the vessel is filled, the dosing pump conducts its output, from a certain point in time, back along a retarding ramp 30 until the stoppage 32 of the dosing pump, in order to meter as accurately as possible the desired quantity. At this moment, the pressure initially drops, because the suction pressure at the tip of the pipette is no longer present, until it levels-out towards the end of the dosing operation to a constant range, which is dependent on the liquid column in the vessel. At the beginning of the retarding ramp 30, there is nevertheless a further increase in the pressure p, since a slowing-down of the pressure can still be set in dependence on the viscosity of the liquid to be metered. Equally, in dependence on the viscosity, the pressure profile over the time t, illustrated in FIG. 2 in the lower region, can extend in a considerably flatter manner, so that, for example, sometimes no fall in pressure can be set after the beginning of the retarding ramp.

Therefore, for the evaluation of the dosing operation, a development of the pressure p with respect to time of a gas 10 present in the vessel 20 is initially detected at least periodically during the dosing operation. This development with respect to time (illustrated as the lower curve in FIG. 2) is compared with a desired value development of at least one pump rate or pump output of the dosing pump 22, defining the dosing operation. The comparison result then leads to the evaluation criterion, whereby a plurality of error conditions are used for the evaluation of the dosing operation, which conditions consider the pressure development in a time window $\Delta t$ after a prescribed change in the defining pump rate or pump output. These values are present or respectively are prescribed as control variables, and are, in consequence, known to the control unit 23. In FIG. 2, the rate development 35 of the pump plunger of the dosing pump 22 is illustrated. These values are correlated with one another, in order to produce thereby evaluation conditions, after a desired/actual comparison, and to make available an evaluation result of the dosing operation.

Through the use of various values, namely the values of the pressure p or of the temperature on the one hand and, on the other hand, the values of the pump rate or of the pump output respectively over time, a desired value range or desired value development respectively is produced, which is multi-dimensional. Thus, a desired value window is setup in which both the pump state variables and the pressure or the temperature of the gas are to move, so that a dosing operation can be evaluated as successful. The dosing operation is evaluated as faulty or in need of correction when it is determined that the detected development, with respect to time, of the pressure p or of the temperature lies outside a desired value range, at least in sections, with a prescribed pump rate or prescribed pump output.

The obtained pressure or temperature signal, in consequence, can be evaluated in conjunction with the development of the pump state variable as follows, each of the following error conditions also being able to be checked on its own as an exclusion criterion, but a plurality of error conditions are checked:

1. Rise in Pressure or Change in Temperature

The delay between the starting 31 of the dosing pump and the increase t1 in the pressure p or the change in the temperature T is determined and may not exceed a limit value $\Delta t1$. If this limit value is exceeded, an error message is produced. The pressure increase or the temperature change is usually determined by calculating the first deviation of the pressure signal or of the temperature signal respectively, while the starting time of the dosing pump 22 is known to the control system. If, in the case of an error, only air is drawn-in, no pressure increase and no temperature change respectively can be determined. Through the vertical readjustment of the pipette, the contact with the fluid can then initially still occur. In this case, the pressure increase or the temperature change respectively is delayed. If there is no pressure increase or no temperature change respectively, an error condition exists. Mostly, the vertical readjustment of the vessel 20 is forcibly controlled by a stepping motor, but basically even a regulated readjustment can be effected.

Figure 3:
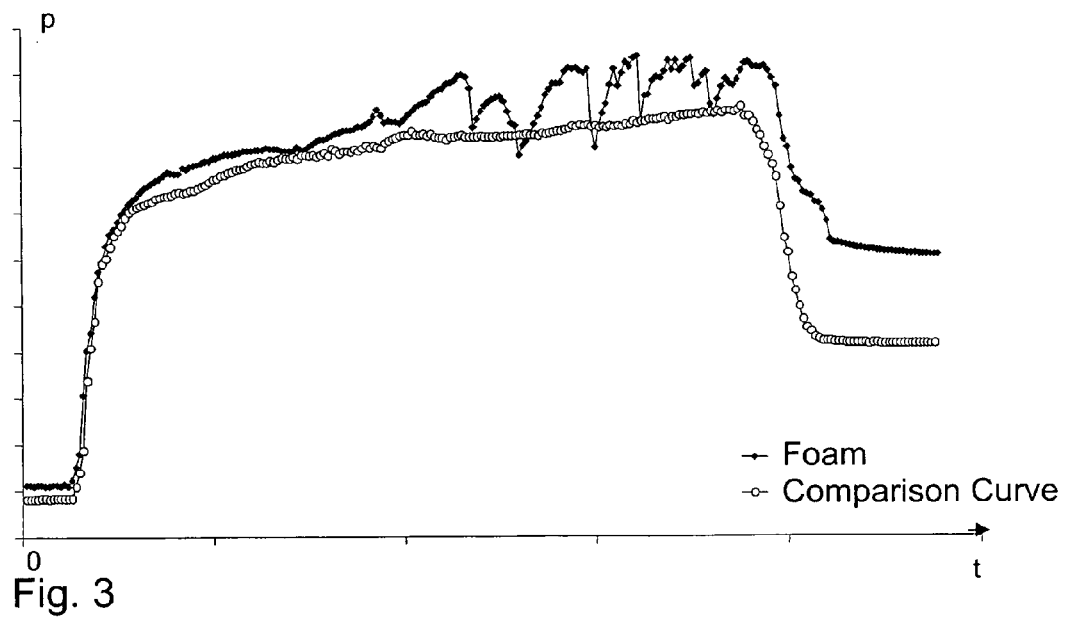
FIG. 3 illustrates a typical pressure development over time during an aspiration of air bubbles/foam relative to a comparison curve.
Figure 5:
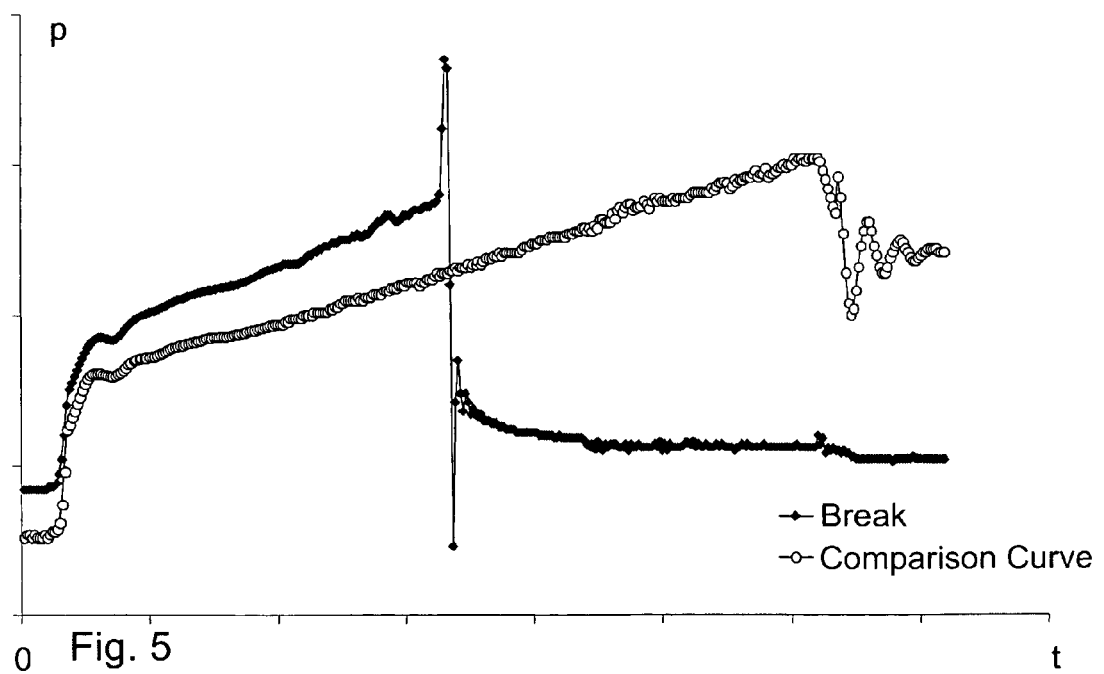
FIG. 5 illustrates a typical pressure development with an inadequate readjustment of the vessel relative to a comparison curve.

2. Monotonically Ascending Pressure Increase or Respectively Monotonic Temperature Change Between the increase in the pressure or respectively the first temperature change at time $t_1$ and at the beginning $t_2$ of the retarding ramp 30 of the dosing pump 22, the pressure p must constantly rise or respectively the temperature must constantly change. The development can be defined as monotonically ascending when each scanning value is greater than the preceding value. This is not the case, for example, in FIG. 3, since the aspiration of air bubbles leads to characteristic discontinuities in the pressure curve, since the flow resistance during the aspiration of air is much smaller than during the aspiration of liquid. More especially, in the case of insufficient vertical readjustment of the pipette, that is to say of the vessel 20, the contact with the liquid can be lost, whereby air is drawn-in. Even in this case, the constant increase in the pressure does not exist, as for example the sketch in FIG. 5 shows.

3. Monotonically Descending Fall in Pressure

According to FIG. 2, the pressure should be monotonically descending after expiry of the time $\Delta t_2$ after the beginning $t_2$ of the retarding ramp 30 of the dosing pump 22 until the stoppage 32 of the dosing pump 22, for which purpose the calculation of the first deviation is suitable. Through the criterion monotonically descending, each pressure increase is detected until the switching-off of the dosing pump. Relatively small coaglutinates or foreign bodies, which pass through the intake opening of the pipette, allow the pressure to rise briefly.

4. Time of the Fall in Pressure

The time $\Delta t_2$ between the beginning $t_2$ of the retarding ramp 30 of the dosing pump 22 until the actual fall in the pressure p must not exceed a limit value. More especially in conjunction with criterion 1), a condition can be defined, in consequence, via the length of the aspiration operation, which cannot be defined solely by consideration of the pressure development. If there is too long a period until the fall in pressure, the metered quantity is to be rejected.

5. Maximum Pressure

Figure 4:
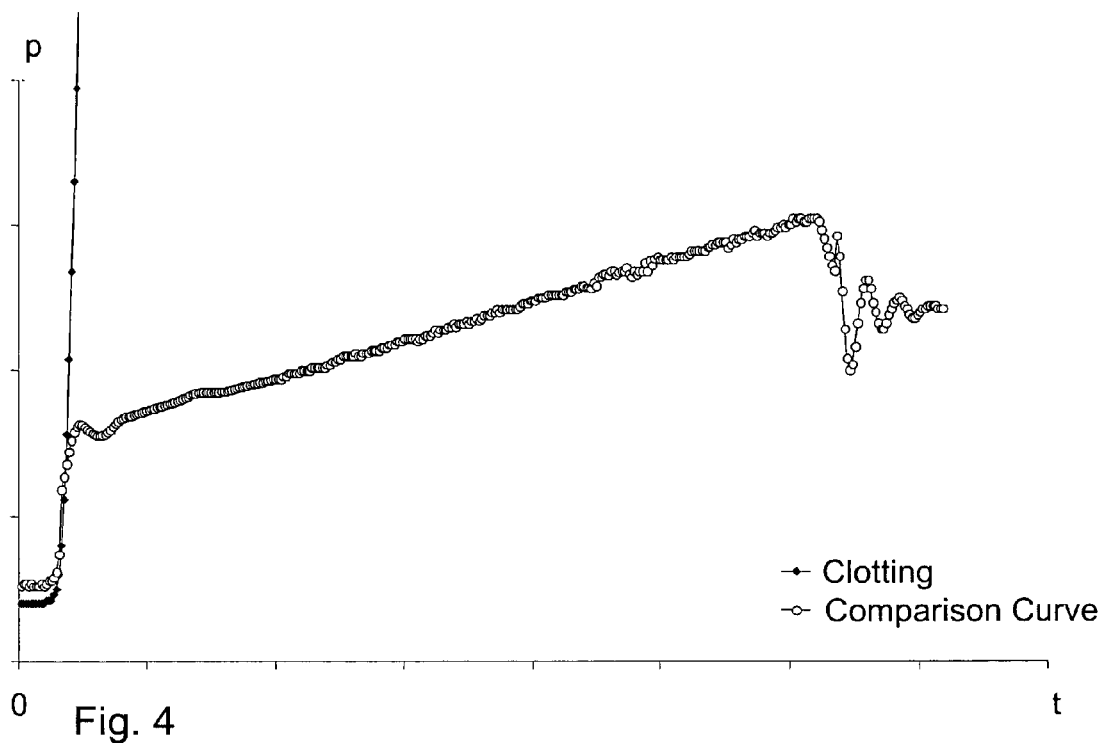
FIG. 4 illustrates a typical pressure development over time in the event of a blockage relative to a comparison curve.

At the time of the beginning $t_2$ of the retarding ramp 30 of the dosing pump 22, the pressure should move in a specific tolerance range 33. A maximum pressure p_max should not be exceeded. Large coaglutinates, high-viscous liquids or a blocked intake opening of the pipette, as for example in FIG. 4, produce an excessive pressure increase and can be detected by a limit value at this time. At the same time, at the beginning of the retarding ramp 30, the pressure should be greater than a minimum limit value p_min. A partial drawing-in of air, air bubbles or a leak in the pipette result in too low a pressure. The characteristic point of the starting of the retarding ramp 30 is selected as the time for checking, since a large part of the volume here is already drawn-in, and the flow resistance is consequently at its maximum.

6. Delay Time Until Constant Pressure or Until Constant Temperature

The delay $\Delta t_{const}$ between the end 32 of the pump movement and achieving a constant pressure or a constant temperature is defined, and should not exceed a limit value. Liquids with too high a viscosity or a partial blockage of the intake opening of the vessel 20 retard the fall in pressure or the achievement of a constant temperature at the end of the intake operation, and can be recognized by exceeding a limit value with respect to time.

7. Static Final Pressure or Static End Temperature Respectively

If criterion 6. that is to say $\Delta t_{const}$, is not exceeded, the value, existing in the case of constant pressure or constant temperature at the end of the dosing operation, must lie within a tolerance range 34. At the end of the intake operation, the pressure or the temperature is still only dependent on the static value of the liquid column. When using the pressure, the value is a parameter for the drawn-in volume. In consequence, the usability of the sample can be evaluated.

Through the detection of the pressure p or of the temperature by means of a sensor, and through prescribing the pump rate or the pump output of the dosing pump 22, possibilities are therefore created for defining the dosing operation not only on the basis of the pressure of the medium but also on the basis of a further variable, which is independent of this pressure or temperature. This leads more especially to leakages being shown more clearly or respectively to readjustments being able to be made even more rapidly, more especially at the beginning and at the end of the dosing operation. In addition, criteria are provided which are not to be recognized by a pressure or temperature observation alone and, in consequence, render possible a sometimes even premature recognition of an incorrect dosage. The control unit 23 picks-up the values in its data storage means 25, so that, via the data processing unit 27, evaluation criteria can be produced in order to evaluate the dosing operation.

An alternative to prescribing the pump rate or output may reside in prescribing another variable such as, for example, the current consumption of the pump or the volumetric flow of the medium, and to control the pump in dependence thereon. This would have the consequence that that variable must be prescribed, and the pump development must be measured parallel to the pressure.

The detection of the pressure p of the gas in the vessel is effected via a by-pass duct 28, communicating with the gas in the vessel 20 and being provided on the holder 11 of the vessel. The by-pass duct permits an immediate measurement of pressure changes in the vessel, without having to refer to measurements of changes in the medium. This by-pass duct is not, therefore, a mere T-shaped part—as is usual in prior art—wherein, because of the direct branching-off from the intake duct 19, the medium in the vessel and pump must be identical, so that the T-shaped part can be used to connect with the pressure sensor. Instead, with the use of a by-pass duct, the medium between pump 22 and vessel 20 can be different from that in the by-pass duct, e.g. the medium in the pump may be a system liquid. This is advantageous because, in consequence, the volume in the pump and supply lines (hoses) can be filled with incompressible liquid, and this increases the accuracy of the liquid intake. However, the medium in the vessel 20 should be air, because the vessel in the form of a single-use pipette is replaced for each transfer. Only this type of measuring duct renders possible the measurement of the pressure in the vessel with the simultaneous use of system liquid. By this means, the pressure can be measured independently of the medium via which the dosing pump 22 produces the reduced pressure in the vessel 20. In consequence, a liquid medium can be used in the same way as a gaseous medium for this purpose, and such increases the possible uses of the apparatus.

Figure 6:
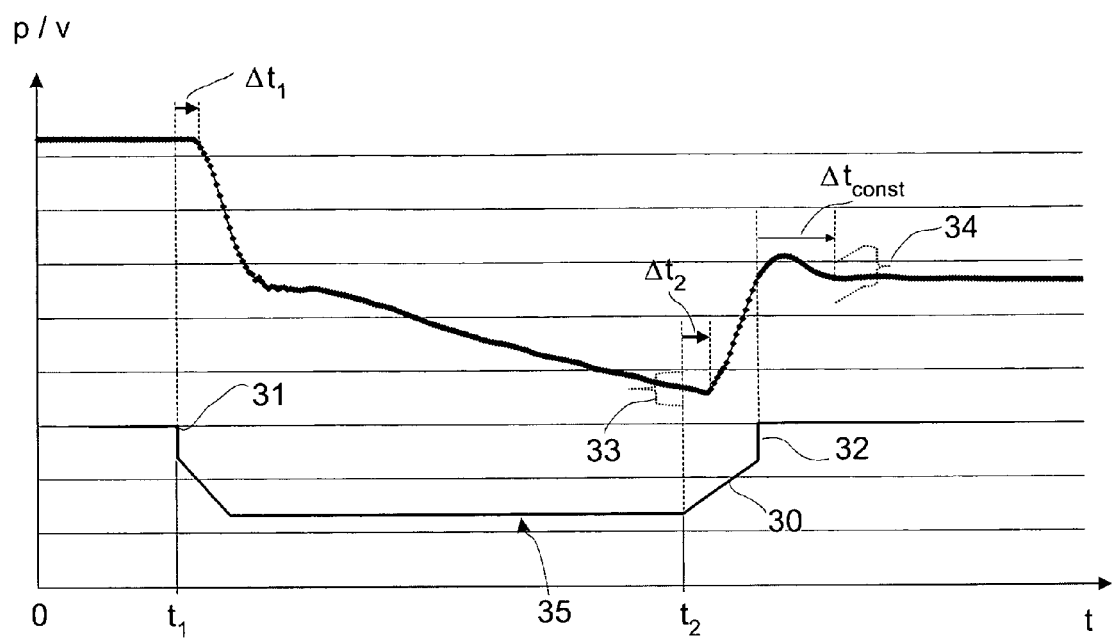
FIG. 6 illustrates a typical pressure development a dispense process, superimposed with the rate development of the pump.

The seven conditions mentioned relate to an aspirating operation, but they may be transferred to the dispensing operation illustrated in FIG. 6 with reversed signs. The reference numerals in FIG. 6 are identical to those in FIG. 2. Thus, the monitoring of a pressure rise during the aspirating operation corresponds to a monitoring of a pressure fall during in the case of dispensing. In FIG. 6 again, the rate development 35 of the pump plunger of the dosing pump 22 is illustrated. Shown are starting 31, retarding ramp 30 and stoppage 32 of the dosing pump 22.

In analogy to FIG. 2, also FIG. 6 shows a delay between the starting 31 of the dosing pump and the drop $t_1$ in the pressure p, which delay may not exceed a limit value $\Delta t_1$. If this limit value is exceeded, an error message is produced. Additionally, between the increase in the pressure at time $t_1$ and at the beginning $t_2$ of the retarding ramp 30 of the dosing pump 22, the pressure p must constantly fall. The development can be defined as monotonically falling when each scanning value is smaller than the preceding value. This is not the case, for example, with air bubbles and leads to an error condition.

According to FIG. 6, the pressure should be monotonically ascending after expiry of the time $\Delta t_2$ after the beginning $t_2$ of the retarding ramp 30 of the dosing pump 22 until the stoppage 32 of the dosing pump 22, for which purpose the calculation of the first deviation is suitable. Through the criterion monotonically ascending, each pressure increase is detected until the switching-off of the dosing pump. Relatively small coaglutinates or foreign bodies, which pass through the intake opening of the pipette, allow the pressure to fall briefly. The time $\Delta t_2$ between the beginning $t_2$ of the retarding ramp 30 of the dosing pump 22 until the actual rise in the pressure p must not exceed a limit value. More especially in conjunction with the starting delay of the dosing pump 22, a condition can be defined, in consequence, via the length of the aspiration operation. At the time of the beginning $t_2$ of the retarding ramp 30 of the dosing pump 22, the pressure should move in a specific tolerance range 33. A maximum pressure p_max should not be exceeded. At the same time, at the beginning of the retarding ramp 30, the pressure should be greater than a minimum limit value p_min.

The delay $\Delta t_{const}$ between the end 32 of the pump movement and achieving a constant pressure is defined, and should not exceed a limit value. Liquids with too high a viscosity or a partial blockage of the intake opening of the vessel 20 retard the rise in pressure at the end of the intake operation, and can be recognized by exceeding a limit value with respect to time. If $\Delta t_{const}$ is not exceeded, the value, existing in the case of constant pressure at the end of the dispense operation, must lie within a tolerance range 34. At the end of the dispense operation, the pressure is still only dependent on the static value of the liquid column.

The pressure is referenced to the ambient pressure or—in better words to the pressure existing prior to the pump action during the aspirating operation as well as during the dispensing operation. Thus, all pressure measuring values are preferably referenced to the pressure prior to the pump action. In dispensing the liquid, however, the pressure has not to fall back to this reference pressure, especially if only a part of the liquid is dispensed.

As already initially mentioned, the temperature may be used and evaluated instead of the pressure. A liquid aspirating operation or liquid dispensing operation is usually a fast process, at least fast compared with a temperature compensation between the gas enclosed in the vessel and its environment. Therefore, the following equations known in physics for adiabatic change of state of ideal gases can approximately be used. These equations show the interrelation between volume, pressure and temperature.

$$p_1 * V_1^x = p_2 * V_2^x \quad (1)$$

$$\frac{T_2}{T_1} = \left(\frac{p_2}{p_1}\right)^{\frac{x-1}{x}} \quad (2)$$

The values pressure $p_1$, volume $V_1$, temperature $T_1$ describe the initial state before the aspiration process. The values pressure $P_2$, volume $V_2$, temperature $T_2$ describe any arbitrary later point in time after a change of state. Value x is a constant specific for a certain gas. In the case of air 1,402.

In the aspirating or dispensing operation the dosing pump causes a change in volume. The initial volume $V_1$ is compressed or expanded to volume $V_2$. Equation (1) shows, how the pressure changes as a consequence thereof. At the same time the temperature changes as can be seen in equation (2). This equation shows that the pressure development is associated with a temperature development comprising the same qualitative characteristics. Rising pressure corresponds to rising temperature and vice versa. Therefore, the detection and evaluation of the temperature development is equally adapted as the pressure measurement and leads to a graph of temperature over time which is essentially analogue to the figures showing the pressure development.

A preferred purpose of use is a pipetting system or apparatus which carries out an appropriate aspirating and/or dispensing operation during the pipetting process.

It is self-evident that this description can be subjected to the most varied modifications, changes and adaptations which are within the range of equivalents to the accompanying claims.

The invention claimed is:

1. Method of evaluating a dosing operation, carried out by means of a dosing pump, for dosing a liquid medium in a vessel, filled at least partially with a gas, said method comprising:
   detecting a development, with respect to time, of a pressure or of a temperature of the gas present in the vessel at least periodically during the dosing operation,
   comparing a detected development, with respect to time, of the pressure or of the temperature, with a desired value development, prescribed for a control unit of the dosing pump, of a pump rate or pump output determining the dosing operation, and
   issuing an evaluation result in dependence on the determined comparison,
   wherein the dosing operation is evaluated to be faulty or in need of correction when it is determined that at least a portion of the detected development, with respect to time, of the pressure or of the temperature with the prescribed pump rate or prescribed pump output lies outside a desired value range, and
   wherein a plurality of error conditions for the evaluation of the dosing operation are used, which consider the development of the pressure or of the temperature in a time window after a prescribed change in the defining prescribed pump rate or pump output.

2. Method according to claim 1, wherein the pump rate or the pump output is prescribed by a prescribed development of one parameter, defining the pump rate or the pump output, and the pump output or the pump rate is controlled according to the parameter.

3. Method according to claim 1, wherein, as an error condition, it is examined whether a time between a staffing of the dosing pump and at least one of a rise and fall in the pressure or in a change in the temperature exceeds a limit value.

4. Method according to claim 1, wherein, as an error condition, it is examined whether a time between a beginning of a retarding ramp of the dosing pump and an actual drop or an actual rise in the pressure or in a change in the temperature exceeds a limit value.

5. Method according to claim 1, wherein, as an error condition, it is examined whether the pressure is not monotonically ascending or monotonically falling between a rise in the pressure or a staffing of the dosing pump and a beginning of a retarding ramp.

6. Method according to claim 1, wherein, as an error condition, it is examined whether the change in the temperature is not monotonic between a rise or fall in the temperature or a staffing of the dosing pump and a beginning of a retarding ramp.

7. Method according to claim 1, wherein, as an error condition, it is examined whether the pressure or the temperature at the beginning of a retarding ramp does not exceed a maximum value and is not smaller than a minimum limit value.

8. Method according to claim 1, wherein, as an error condition, it is examined whether the pressure is not monotonically descending respectively falling after a time has passed after the beginning of a retarding ramp of the dosing pump until a stoppage of the dosing pump.

9. Method according to claim 1, wherein, as an error condition, it is examined whether the temperature is not monotonically changing after a time has passed after the beginning of a retarding ramp of the dosing pump until a stoppage of the dosing pump.

10. Method according to claim 1, wherein the dosing operation is at least a part of an aspirating operation during the pipetting process.

11. Method according to claim 1, wherein the dosing operation is at least a part of a dispensing operation during the pipetting process.

12. Method according to claim 1 wherein the gas is air.

13. Method according to claim 1, wherein, as an error condition, it is examined whether a limit value with respect to time, is exceeded between an end of the pump action and reaching a constant pressure or a constant temperature.

14. Method according to claim 13, wherein, as an error condition, it is examined whether the constant pressure, being set during the limit value with respect to time towards the end of the dosing operation, lies within a tolerance range.

15. Method according to claim 13, wherein, as an error condition, it is examined whether the constant temperature, being set during the limit value with respect to time towards the end of the dosing operation, lies within a tolerance range.

16. Method according to claim 1, wherein the pressure in the vessel is detected via a separate by-pass duct.

17. Method according to claim 16, wherein the pressure in the by-pass duct is measured independently of an intake duct for aspiring or dispensing the liquid medium.

18. Method according to claim 16, wherein a medium, which differs from the liquid medium, is used as a system medium for aspiring or dispensing the liquid medium.

19. Apparatus for evaluating a dosing operation comprising
   a vessel filled at least partially with a gas,
   a dosing pump for dosing a liquid medium into the vessel,
   at least one detector for detecting a development, with respect to time, of a pressure or of a temperature of the gas, present in the vessel, at least periodically during the dosing operation, a control unit for controlling a prescribed pump rate or a prescribed pump output of the dosing pump with a desired value development of the prescribed pump rate or the prescribed pump output for determining the dosing operation, an comparator for comparing a detected development, with respect to time, of the pressure or of the temperature, with the desired value development of the prescribed pump rate or pump output, an evaluation unit for evaluating in dependence on the determined comparison the dosing operation to be faulty or in need of correction when it is determined that at least a portion of the detected development, with respect to time, of the pressure or of the temperature with the prescribed pump rate or prescribed pump output lies outside a desired value range, in using a plurality of error conditions for the evaluation unit, the error conditions consider the development of the pressure or of the temperature in a time window after a prescribed change in the defining prescribed pump rate or pump output.

20. Apparatus according to claim 19, wherein the evaluation unit comprises examination means for examining as error condition whether a time between a starting of the dosing pump and at least one of a rise and fall in the pressure or in the change in the temperature exceeds a limit value.

21. Apparatus according to claim 19, wherein the evaluation unit comprises examination means for examining as error condition whether a time between a beginning of a retarding ramp of the dosing pump and an actual drop or an actual rise in the pressure or a change in the temperature exceeds a limit value.

22. Apparatus according to claim 19, wherein the evaluation unit comprises examination means for examining as error condition whether the pressure is not monotonically ascending or monotonically falling between a rise in the pressure or a staffing of the dosing pump and a beginning of a retarding ramp.

23. Apparatus according to claim 19, wherein the evaluation unit comprises examination means for examining as error condition whether the change in the temperature is not monotonically changing between a change in the temperature or a staffing of the dosing pump and a beginning of a retarding ramp.

24. Apparatus according to claim 19, wherein the evaluation unit comprises examination means for examining as error condition whether the pressure or the temperature at the beginning of a retarding ramp does not exceed a maximum value and is not smaller than a minimum limit value.

25. Apparatus according to claim 19, wherein the evaluation unit comprises examination means for examining as error condition whether the pressure is not monotonically descending respectively falling after a time has passed after the beginning of a retarding ramp of the dosing pump until a stoppage of the dosing pump.

26. Apparatus according to claim 19, wherein the evaluation unit comprises examination means for examining as error condition whether the temperature is not monotonically changing after a time has passed after the beginning of a retarding ramp of the dosing pump until a stoppage of the dosing pump.

27. Apparatus according to claim 19, wherein a separate by-pass duct is provided for detecting the pressure in the vessel independently of an intake duct for aspiring or dispensing the liquid medium.

28. Apparatus according to claim 27, wherein a medium, which differs from the liquid medium, is used as a system medium for aspiring or dispensing the liquid medium.

29. Apparatus according to claim 19, wherein the evaluation unit comprises examination means for examining as error condition whether a limit value, with respect to time, is exceeded between an end of the pump action and reaching a constant pressure or a constant temperature.

30. Apparatus according to claim 29, wherein the evaluation unit comprises examination means for examining as error condition whether the constant pressure, being set during the limit value with respect to time towards the end of the dosing operation, lies within a tolerance range.

31. Apparatus according to claim 29, wherein the evaluation unit comprises examination means for examining as error condition whether the constant temperature, being set during the limit value with respect to time towards the end of the dosing operation, lies within a tolerance range.

* * * * *